(12) United States Patent
Wang et al.

(10) Patent No.: US 12,337,041 B2
(45) Date of Patent: Jun. 24, 2025

(54) MEDICAL IMAGING TECHNIQUE USING X-RAY TO NEAR-INFRARED DOWNCONVERTING NANOPOWDER

(71) Applicant: THE TRUSTEES OF DARTMOUTH COLLEGE, Hanover, NH (US)

(72) Inventors: Xiaoxin Wang, Hanover, NH (US); Jifeng Liu, Hanover, NH (US); Shudong Jiang, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 1043 days.

(21) Appl. No.: 17/322,577

(22) Filed: May 17, 2021

(65) Prior Publication Data
US 2021/0353778 A1    Nov. 18, 2021

Related U.S. Application Data (60) Provisional application No. 63/025,853, filed on May 15, 2020.

(51) Int. Cl.
*A61K 49/00* (2006.01)
*A61B 5/00* (2006.01)

(52) U.S. Cl.
CPC ........ *A61K 49/0065* (2013.01); *A61B 5/0073* (2013.01)

(58) Field of Classification Search
CPC .......................... A61K 49/0065; A61B 5/0073
See application file for complete search history.

(56) References Cited

U.S. PATENT DOCUMENTS

2017/0000887 A1*  1/2017  Zhang ...................... B82Y 5/00
2019/0168015 A1*  6/2019  Bourke, Jr. ............ A61N 5/062

OTHER PUBLICATIONS

A. M. Smith et al. "Second window for in vivo imaging", Nature Nanotechnogy, vol. 4, Nov. 2009, pp. 710-711.

J. Xu et al., "Recent advances in near-infrared emitting lanthanide-doped nanoconstructs: Mechanism, design and application for bioimaging", Coordination Chemistry Reviews 381, 2019, pp. 104-134.

Z. Xue et al., "X-Ray-Activated Near-Infrared Persistent Luminescent Probe for Deep-Tissue and Renewable in Vivo Bioimaging", ACS Applied Materials & Interfaces, 9, 2017, pp. 22132-22142.

Z. J. Li et al., "In Vivo Repeatedly Charging Near-Infrared-Emitting, Mesoporous $SiO_2/ZnGa_2O_4:Cr^{3+}$ Persistent Luminescence Nanocomposites", Advanced Science, 2, 2015, 6 pages.

Z. J. Li et al. "Direct Aqueous-Phase Synthesis of Sub-10 Nm "Luminous Pearls" with Enhanced in Vivo Renewable Near-Infrared Persistent Luminescence". Journal of the American Chemical Society, 137, 2015, pp. 5304-5307.

T. Maldiney et al., "The in vivo activation of persistent nanophosphors for optical imaging of vascularization, tumours and grafted cells". Nature Materials, vol. 13, 2014, pp. 418-426.

S. Kück, "Laser-related spectroscopy of ion-doped crystals for tunable solid-state lasers", Applied Physics B Lasers and Optics, 72, 2001, pp. 515-562.

K. E. Miyano et al., "Cr K edge X-ray absorption study of Cr dopants in $Mg_2SiO_4$ and $Ca_2GeO_4$", Applied Physics Letters, 71, 1998, pp. 1168-1170.

M. F. Hazenkamp et al., "Optical spectroscopy of Cr4+ -doped Ca2GeO4 and Mg2SiO4", Physical Review B, vol. 53, No. 5, 1996, pp. 2367-2377.

P. Sujatha Devi et al., "Sol-gel syntheses and spectroscopic characterization of chromium-doped silicates and germanates", Chem. Mater. 12, 2000, pp. 1378-1385.

D. Reinen et al., "Cr4+ in Tetrahedral Coordination of Oxide Solids: A Spectroscopic and Structural Investigation", Inorg. Chem. 34, 1995, pp. 184-192.

V. Petričević et al., "Room-temperature near-infrared tunable laser operation of $Cr^{4+}:Ca_2GeO_4$", Optics Letters. Vol. 21, No. 21, Nov. 1, 1996, pp. 1750-1752.

(Continued)

*Primary Examiner* — Robert S Cabral
(74) *Attorney, Agent, or Firm* — Cozen O'Connor (57) ABSTRACT

A phosphor excitable by X-ray and blue-light emits light in the near-infrared (NIR-II, 1000-1700 nanometers) forms nanoparticles less than 200 nanometers diameter. The nanoparticles are tagged by coating with silica, then conjugating with polyethylene glycol (PEG) and tissue-selective compounds such as antibodies, nucleic acid chains, and other ligands. In embodiments, we administer the tagged nanoparticles to a subject, then localize the nanoparticles, and thus antigen-bearing tissues, by irradiating the subject with X-ray or other radiation beams while imaging near infrared light emitted from the subject. The nanoparticles are made by mixing 1-50 micron calcium oxide and germanium oxide powders with dilute nitric acid, adding chromium (III) nitrate at a ratio to germanium between 0.001 and 0.1, adding tartaric acid solution with molar ratio to metal ions between 1~10, and adjusting pH to 0.1-4 with nitric acid, then later heating to form a sol, oven drying, and calcinating the sol.

16 Claims, 11 Drawing Sheets

(56) References Cited

OTHER PUBLICATIONS

A. D. Dayan et al., "Mechanisms of chromium toxicity, carcinogenicity and allergenicity: review of the literature from 1985 to 2000". Human & Experimental Toxicology, 20, 2001, pp. 439-451.

M. I. Tombak et al., "Some luminescence properties of sodium zinc germanate", UDC 535.37, 1535-1537 (1973), translated from Zhurnal Prikladnoi Spectroskopii, vol. 13, No. 5, Nov. 1970, pp. 921-923.

Y. Tang et al., "Structure, microwave dielectric properties, and infrared reflectivity spectrum of olivine type $Ca_2GeO_4$ ceramic", Journal of the European Ceramic Society, 39, 2019, pp. 2354-2359.

L. L. Isaacs, "Preparation of Submicron and Micron Size Cr (Iv) Optical Composites", Mat. Res. Soc. Symp. Proc. vol. 581, 2000, pp. 411-414.

T. Malcherek et al., "Structure and phase transition of $CaGe_2O_5$ revisited", Phys. Chem. Minerals. 31, 2004, pp. 224-231.

L. V. Ermakova et al., "Towards a new group of olivine-type afterglow phosphors: the case of Ca2GeO4: Dy3+", Materials Letters, 2018, pp. 233, 39-41.

T. Wang et al., "Self-activated long persistent luminescence from different trapping centers of calcium germanate", Opt. Express vol. 23, No. 10, May 2015, pp. 12595-12604.

\* cited by examiner

MEDICAL IMAGING TECHNIQUE USING X-RAY TO NEAR-INFRARED DOWNCONVERTING NANOPOWDER

CROSS-REFERENCE TO RELATED APPLICATIONS

This application claims the benefit of priority from U.S. Patent Application No. 63/025,853, filed May 15, 2020, which is incorporated herein by reference in its entirety.

BACKGROUND

Magnetic nanoparticles have been tagged with antibodies and other tissue-selective compounds. When these nanoparticles are administered to a subject, they may localize in particular tissues, such as cancer tissues, of interest to physicians. These magnetic nanoparticles can then be located to an extent by scanning the subject with magnetic fields and using specialized electronics. Resulting images are imperfect but can be useful in locating and evaluating extent of the tissues in which the nanoparticles localize.

Near-infrared (NIR) light penetrates living mammalian tissue much more readily with less scattering and absorption than do shorter wavelengths of light, such as blue visible light. Therefore, NIR bioimaging offers the advantages of deep tissue penetration, high temporal and spatial resolution, and minimal autofluorecence.

SUMMARY

We developed a phosphor excitable by X-ray and blue-light electromagnetic radiation that, when excited, emits light in the near-infrared (NIR-II, 1000-1700 nanometer (nm)) range.

In embodiments we have formed the phosphor into nanoparticles of size 5-200 nanometers diameter, the nanoparticles of this phosphor are also known herein as the nanophosphor.

In embodiments we have formed tagged nanoparticles by coating the phosphor-containing 5-200 nanometer diameter nanoparticles first with silica, then conjugating the silica-coated phosphor-containing nanoparticles with polyethylene glycol (PEG) and tissue-selective compounds including antibodies, nucleic acid chains, and other ligands.

In embodiments, we propose administering the tagged nanoparticles to a subject, then locating the nanoparticles in the subject by irradiating the subject with focused X-ray or other radiation beams while imaging near infrared light emitted from the subject.

BRIEF DESCRIPTION OF THE FIGURES

FIGS. 6A, 6B, and 6C illustrate the optical properties of $Ca_2GeO_4$:0.05 Cr nanophosphor material.

DETAILED DESCRIPTION OF THE EMBODIMENTS

We disclose an efficient X-ray downconverter containing non-toxic, tetravalent-Cr doped $Ca_{2-x}M_xGe_{1-y}N_yO_4$ (M=Mg, Sr, Ba, Zn and N=Si, Sn) nanophosphor that converts X-ray radiation into emission in the near-infrared II (NIR-II, 1000~1700 nm) range for optical bio-imaging diagnosis and treatment. One example is a $Ca_2GeO_4$:$Cr^{4+}$ nanoparticle powder synthesized with minimal organic substance, impurity-free and low-temperature methods. The small size (5~200 nm diameter) of the nanoparticles is desirable to shorten the excretion time in bio-imaging applications. The tetravalent $Cr^{4+}$ ions give a broad emission, covering most of the NIR-II window. The $Ca_2GeO_4$ host includes Ge—$O_4$ tetrahedral structures that can be excited with X-ray, ultraviolet, or visible light and then transfers the energy to $Cr^{4+}$ active emission centers.

The $Cr^{4+}$ ion itself can also be efficiently excited by broad-spectrum Cherenkov light emissions at wavelengths less than 900 nm induced by X-Ray radiation. The thermal release of carriers from the traps in the host generated by X-ray radiation or co-doping allows $Cr^{4+}$ ions to give a persistent afterglow in the NIR-II range. The persistent luminescence after the removal of excitation source can be used to reduce interference by autofluorescence with infrared images and enhance the signal/noise ratio in optical bio-imaging. Therefore, $(Ca,M)_x(Ge,N)_yO_z:Cr^{4+}$ (M=Mg, Sr, Ba, Zn and N=Si, Sn) is a promising X-ray, ultraviolet, and visible light downconversion to NIR-II nanophosphor usable in multimode bio-imaging applications.

The use of the NIR-II light for fluorescence bioimaging to view nanophosphor concentrations offers the advantages of deep tissue penetration, high temporal and spatial resolution, and minimal autofluorescence. NIR II phosphors excited with X-ray, or X-ray induced blue-light Cherenkov emissions, provide new opportunities in the deep-tissue, in-vivo optical bioimaging. X-ray enables unlimited penetration depth in biological tissues and finds wide applications in biomedical imaging, such as computed tomography (CT). The seamless integration of CT and X-ray downconversion NIR fluorescence imaging offers a more reliable multimode bioimaging method for precise diagnosis and surgery. Rare-earth (RE) ion-doped nanostructures have been investigated intensively in different hosts with various rare-earth dopants and co-dopants for biomedical applications. However, a major concern on RE-doped nanoprobes for clinical studies is the potential toxicity and excretion issues. Among the other groups of transition metal (TM) active ions, only $Cr^{3+}$-doped $ZnGa_2O_4$ persistent luminescent nanoparticles are demonstrated for optical bioimaging with emissions at ~700 nm, far below the wavelength of the NIR-II window.

Figure 1:
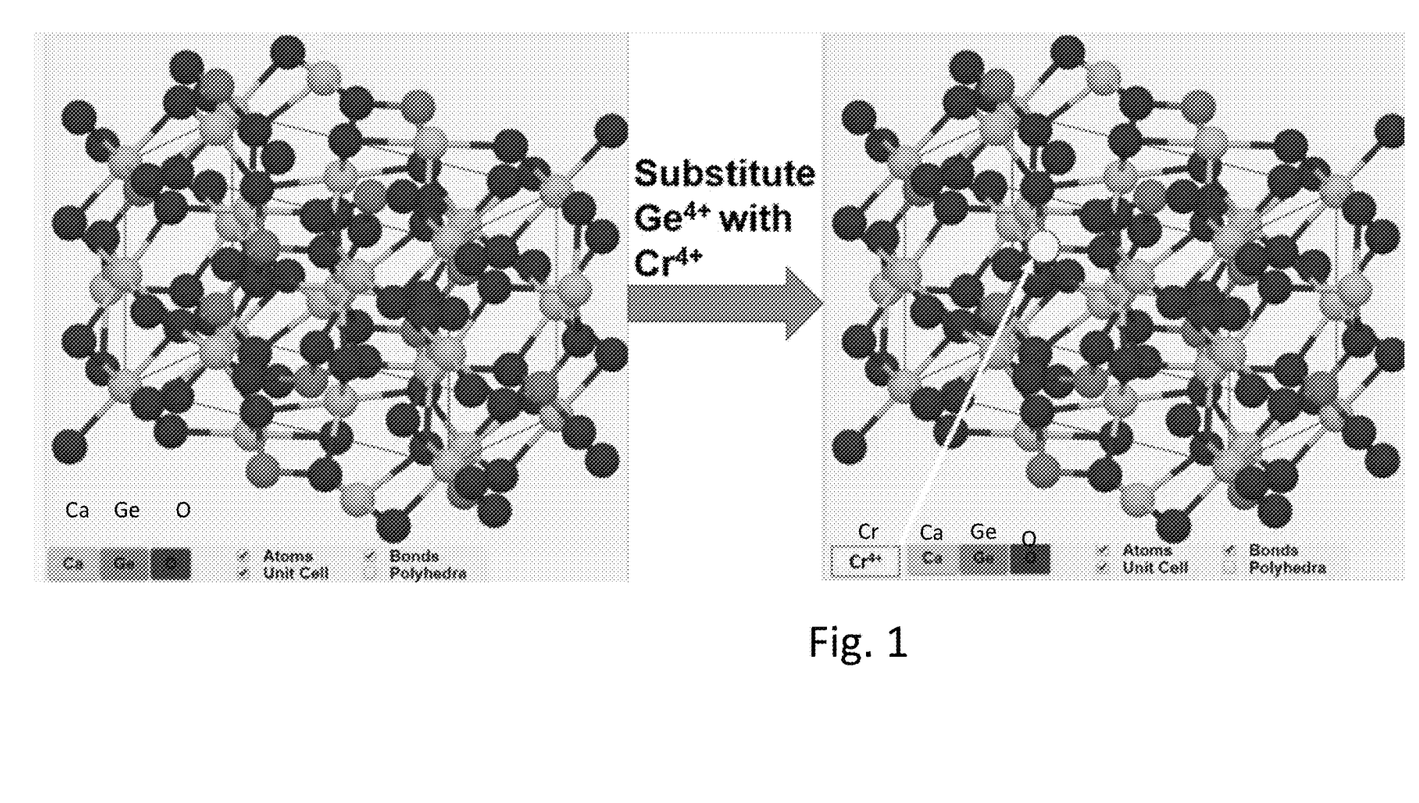
FIG. 1 is a schematic showing partial substitution of $Ge^{4+}$ with $Cr^{4+}$ in a $Ca_2GeO_4$ crystal structure of our X-ray or blue-light excited phosphor in near-infrared NIR-II spectral regime. In some embodiments, remaining Ge atoms are substituted with Si or Sn atoms. Similarly, in some embodiments the Ca atoms can be substituted with Mg, Sr, Ba, or Zn atoms.

Almost all possible TM ions with different coordination numbers and configurations have been doped into single crystals and explored for tunable laser oscillation and optical amplification. A promising active TM ion is tetrahedrally coordinated $Cr^{4+}$ giving emission within the NIR-II window. The broad-band emission of $Cr^{4+}$ ($3d^2$ configuration) comes from the transition from the first excited state $^3T_2$ to the ground state $^3A_2$. $Cr^{4+}$ ions have been incorporated in single crystals for laser oscillation and glass ceramics for optical fiber amplifiers. Considering the substitutional ion size, calcium germinate ($Ca_2GeO_4$) and calcium silicate ($Ca_2SiO_4$) are interesting hosts for $Cr^{4+}$ stabilization. The similarity between ionic radii of $Cr^{4+}$ (0.41 Å) and the tetrahedrally coordinated $Ge^{4+}$ (0.39 Å) in Cr-doped $Ca_2GeO_4$ favors the substitution of the $Ge^{4+}$ with $Cr^{4+}$, as shown in FIG. 1. Similarly, the large difference between the ionic radius of $Ca^{2+}$ (1.00 Å) and $Cr^{3+}$ (0.62 Å) or $Cr^{2+}$ (0.73 Å) inhibits the displacement of $Ca^{2+}$ with $Cr^{3+}$ and thus promote $Cr^{4+}$ substitution of a tetrahedral $Ge^{4+}$ in $Ca_2GeO_4$ and $Si^{4+}$ sites in $Ca_2SiO_4$. Optical spectroscopy and EPR provide strong evidence that only $Cr^{4+}$ resides in $Ca_2GeO_4$ and $Ca_2SiO_4$. Strong and high-efficiency luminescence from $Cr^{4+}$ in single crystal $Ca_2GeO_4$ is reported. The emission intensity of $Cr^{4+}$ activated $Ca_2GeO_4$ is one order of magnitude higher than that of Cr-doped yttrium aluminum garnet (YAG) in the similar excitation condition. $CaGe_2O_4$ single crystal matrix can achieve a quantum yield of 60% from $Cr^{4+}$ emission at 1349 nm.

Among various valences of Cr, hexavalent $Cr^{6+}$ is the ion responsible for most of the toxic reactions that may induce mutagenic and carcinogenic risks due to its solubility in water. It has also been found that the use of $Cr^{3+}$ doped zinc gallate nanoparticles (roughly 50 nm size) brings no acute toxicity in the healthy mice. Instead, $Cr^{3+}$ salts such as chromium polynicotinate and chromium picolinate are used as micronutrients and nutritional supplements that have demonstrated a significant number of health benefits in animals and humans. The fully stabilized and substitutional $Cr^{4+}$ in $Ca_2GeO_4$ or $Ca_2SiO_4$ is not expected to impose any health toxicity. $Cr^{4+}$ active ions could also be excited efficiently by X-ray and X-ray-induced Cherenkov emission. Other compounds containing $Ge-O_4$ tetrahedral structures have been demonstrated to absorb X-Ray and store the energy, which enables persistent afterglow and eliminate autofluorescence in the optical bio-imaging. Therefore, tetravalent-Cr doped $Ca_2GeO_4$ nanoparticles can be used as non-toxic, X-ray excited, NIR II phosphors.

Synthesis of $Ca_2GeO_4$ single crystals or ceramic/glass generally involves a calcination temperature >1200° C. with a conventional solid-state reaction approach. A sol-gel method has been used for fabrication of $CaGe_2O_4:Cr^{4+}$ ceramic powder at 850° C., however, when germanium alkoxide is used as the source of Ge the alkoxide hydrolyses so fast that the control of particle size by controlling the pH of the reaction medium is not feasible. The size of $CaGe_2O_4$ particles synthesized by a sol-gel method starting with metal alkoxides is in the range of 500-1000 nm, which is too large for bioimaging applications. For in vivo bio-imaging applications, we prefer particle size less than 50-200 nm to reduce the excretion time. Calcination is performed in air.

To address the above-mentioned challenges, we focus on tetravalent Cr-doped $(Ca,M)_x(Ge,N)_yO_z:Cr^{4+}$ nanophosphors with diameters <200 nanometers (nm) with less than 5% of Ge substituted with the $Cr^{4+}$ for bioimaging applications. The selection criteria of calcium germinates is that Ge is in four-fold coordination ($Ge-O_4$ tetrahedral structures) suitable for $Cr^{4+}$ substitution and stabilization, such as $Ca_2GeO_4$ and $Ca_2Ge_3O_{11}$. M represents Mg, Sr, Ba, or Zn substituting for Ca by between 0% and 100% and N represents Si or Sn substituting for Ge by 0%-100%. The partial substitution of Ca with M, and Ge with N is beneficial to enhance the emission and allows tuning of the emission wavelength of $Cr^{4+}$. In embodiments, the molar concentration of Cr varies between 0.01 mol. % and 5 mol. %. A simple, low-cost, impurity-free polymeric precursor route is employed to synthesize nanophosphors consisting primarily of $(Ca,M)_x(Ge,N)_yO_z:Cr^{4+}$ nanoparticles based on preparing an aqueous precursor solution of metals followed by adding a water-soluble L-tartaric acid as a combined chelating agent and template medium.

Figure 2:
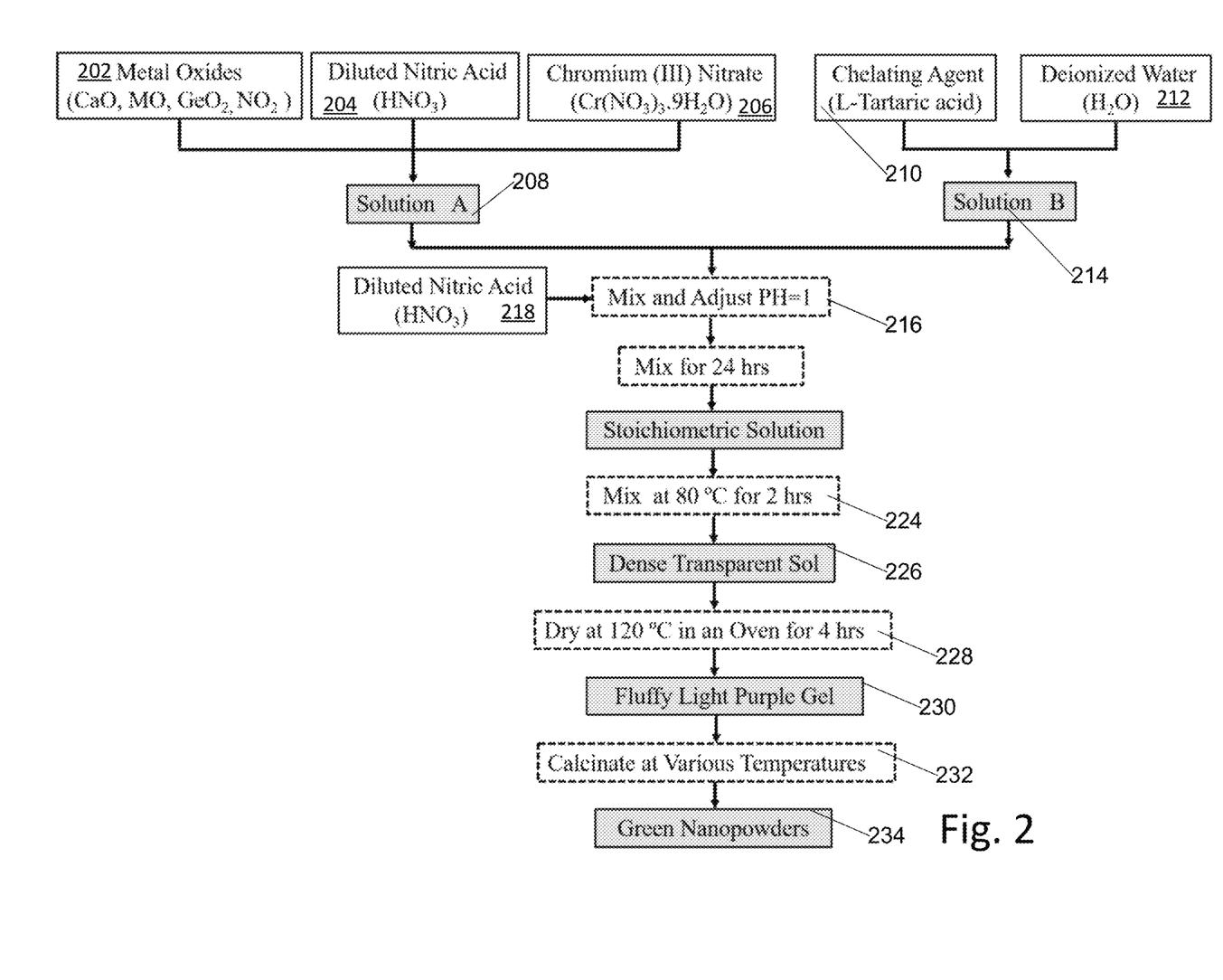
FIG. 2 is a flowchart of the synthesis of nanopowders having the chemical formula tetravalent Cr-doped $(Ca,M)_x(Ge,N)_yO_z:Cr^{4+}$ (M=Mg, Sr, Ba, Zn and N=Si, Sn) from an aqueous precursor solution of metals and additives of water-soluble acid; where Cr=chromium, Mg=magnesium, Sr=strontium, Ba=barium, Zn=zinc, Si=silicon, Sn=tin, O=oxygen, and Ca=calcium as known in the art of chemistry.

In a particular embodiment, the powders according to FIG. 2 were formed as follows:

1. Metal oxide powders 202 (1-50 microns in particle diameter) as raw materials of the host are mixed with diluted nitric acid 204 (4 wt. %~10 wt. %), followed by the addition of chromium (III) nitrate 206 as the starting material of tetravalent Cr dopant (molar ratio of Cr to Ge is 0.001~0.1). The formed solution is named solution A 208.

2. L-tartaric acid 210 is dissolved in deionized water 212 to form solution B 214 with the concentration range of 10 wt. %~50 wt. %. Then two solutions are mixed with the molar ratio of L-tartaric acid in solution B to metal ions in the solution A in the range of 1~10 and stirred for 5-24 hours at room temperature, while pH of the aqueous solution is adjusted 216 to 0.1-4 (in an embodiment 1.0) with diluted nitric acid 218 and mixed for 24 hours. The resulting stoichiometric solution is mixed 224 for another 2~4 hours at 80° C., and in an embodiment 2 hours, to evaporate the water to form a dense transparent sol 226. The sol becomes fluffy light purple gel 230 after 4 hours drying 228 in an oven at 120° C.

3. The gel undergoes a calcination process 232 at various temperatures (700~1000° C.) to form impurity-free green nanopowders. The calcination process involves the decomposition of carbonate and nitrate to remove other elements such as C, H and N, and heat treatment to induce the phase transformations. In this technique, uniform particle size nanopowders 234 are produced due to a homogeneous metal ion distribution in the stoichiometric solution. The synthesis process involves minimal organic substances and produces minimal polluted gas. In a particular embodiment, nanopowder of 20 nanometer average particle size is formed.

Nanophosphors face challenging issues, such as a high density of non-radiative centers due to dangling bonds or other surface states, and the change of local interaction and anisotropic degree of active ions, the preferred location of active ions at the surface. Therefore, surface passivation and co-dopants (such as Mg) are used to passivate or minimize non-radiative centers and promote the substitution with active ions, respectively.

Figure 3:
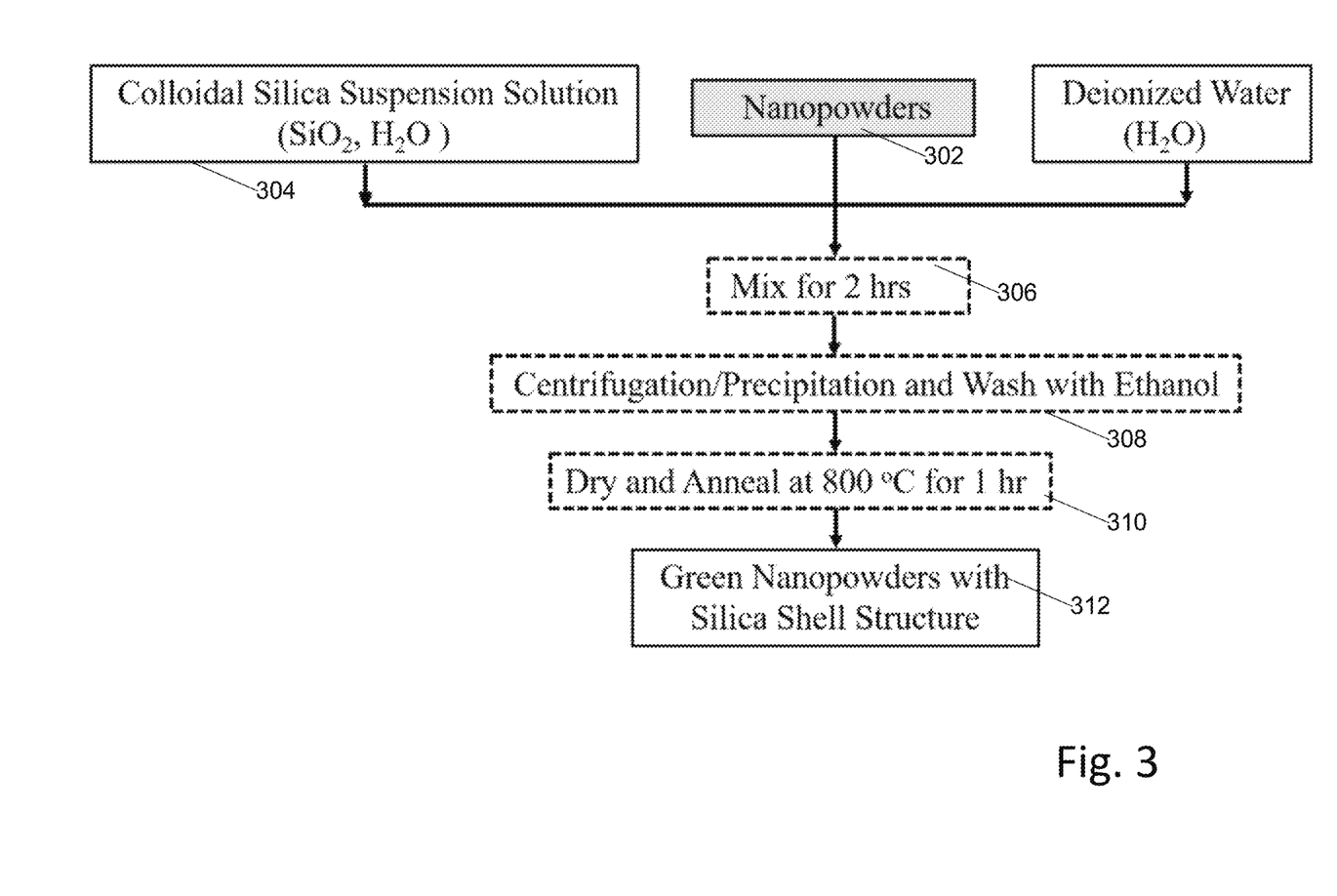
FIG. 3 is a flowchart of a synthesis for silica coating of the $Cr^{4+}$-doped X-ray downconverting nanoparticle powders formed according to FIG. 2.

As an example of surface passivation approaches, the process flow of silica shell structure is described with reference to FIG. 3. Firstly $Ca_2GeO_4$:Cr nanopowder 302 (a nanopowder herein means a powder comprising primarily nanoparticles, and a nanophosphor herein means a nanopowder comprising primarily a phosphorescent material) 302 is dispersed in deionized water with weight ratio nanopowder to water of 0.001~0.02. Then it is mixed 306 with commercial or lab-made colloidal silica suspension solution 304 (silica particle size is 5~20 nm) with a molar ratio of silica to $Ca_2GeO_4$ powder in the range of 0.001~0.1 for 1~2 hours at room temperature. It is followed by a centrifugation/precipitation and washing procedure 308 with ethanol. The final nanopowder 312 with silica shell structure (shell thickness of 5~50 nm) is obtained after drying and annealing 310 at 800° C. for 1 hour.

EXEMPLARY SYSTEMS

In the following, we give six exemplary systems for this invention. Note that the basic concept and methods are not limited to the examples given herein:

Example 1

$Ca_2GeO_4$:Cr Nanophosphor Formation by the Polymerization Sol-Gel Method

Figure 4:
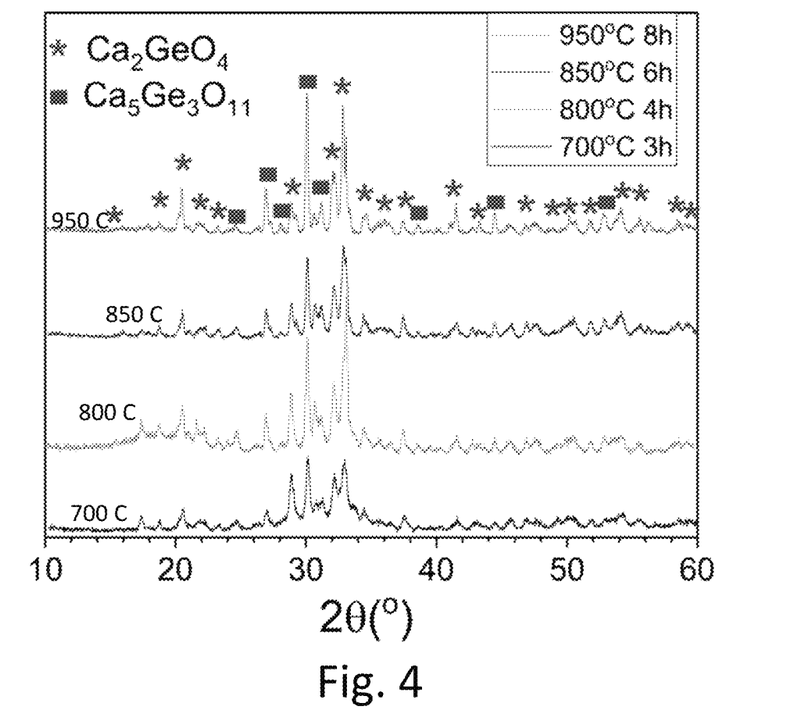
FIG. 4 is an illustration of X-ray diffraction patterns of the $Ca_2GeO_4$:Cr nanophosphor powders obtained at 700° C., 800° C., 850° C. and 950° C. It is a mixture of $Ca_2GeO_4$ crystal phase and $Ca_2Ge_3O_{11}$ crystal phase.

The high-purity starting materials germanium oxide ($GeO_2$) and calcium oxide (CaO) were weighed by the molar ratio Ca/Ge of 2.0 and then dissolved in 4 weight percent (wt. %) diluted nitric acid ($HNO_3$). The starting dopant material $Cr(NO_3)_3$ with the molar ratio Cr/Ge of 0.05 was mixed in the above-mentioned solution. L-tartaric acid was dissolved in de-ionized water to form a solution of 25 wt. %. The two individual solutions were mixed with the molar ratio L-tartaric acid to Ge of 4:1 under constant magnetic stirring for 24 h at room temperature. The pH of the final solution is adjusted to be 2.0 by adding more diluted $HNO_3$. Then the mixture was heated at 80° C. for 2 h under magnetic stirring to form a dense sol. The sol was then heated at 120° C. for 4 h and dried to form a porous purplish precursor. Finally, the precursor was annealed in the air at a temperature between 700~950° C. at a heating rate of 1-10° C./min. The final product is fine greenish powder, indicating the conversion of Cr (III) to Cr (IV). FIG. 4 compares X-ray diffraction patterns of the $Ca_2GeO_4$:Cr nanophosphor powders obtained at different synthesis temperatures and duration. Most peaks are ascribed to $Ca_2GeO_4$ (indicated with *) and the peak broadening suggests the particle size in the nanometer range. $Ca_2GeO_4$ phase begin to form at a temperature of 700° C., much lower than the conventional solid-state-reaction method (1250° C.). Other crystal phase $Ca_5Ge_3O_{11}$ is also identified, but no raw materials ($GeO_2$, CaO or $CaCO_3$) are detected. In both $Ca_2GeO_4$ and $Ca_5Ge_3O_{11}$ hosts, Ge is in tetrahedral sites suitable for $Cr^{4+}$ substitution. Differently, in the orthorhombic structure of $Ca_2GeO_4$, Ge has one type of tetrahedron and Ca is in an octahedral position, while in the triclinic structure of $Ca_5Ge_3O_{11}$, Ge has four different distorted tetrahedral and Ca is in five different octahedra. The different structures of germinate hosts can be used to engineer the $Cr^{4+}$ emission (peak position, spectral width, intensity and persistent afterglow).

Figure 5A:
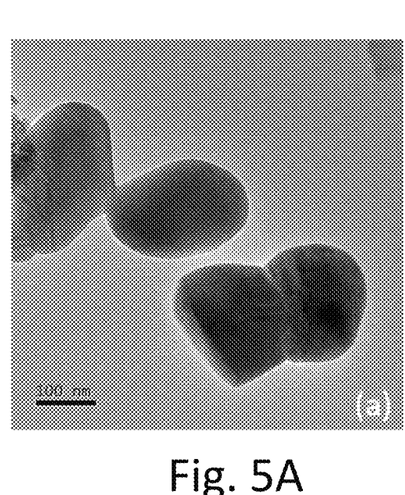
FIGS. 5A and 5B are TEM images of $Ca_2GeO_4$:Cr nanophosphor powders obtained at 950° C.
Figure 5B:
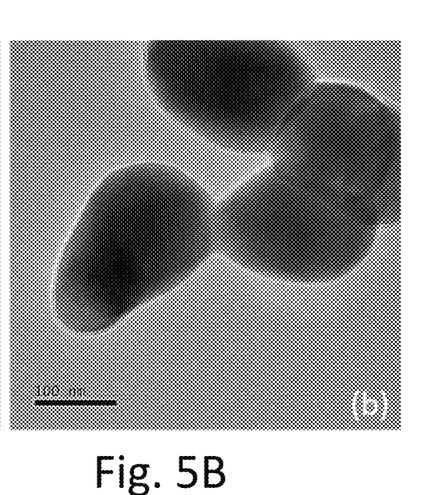
Figure 5C:
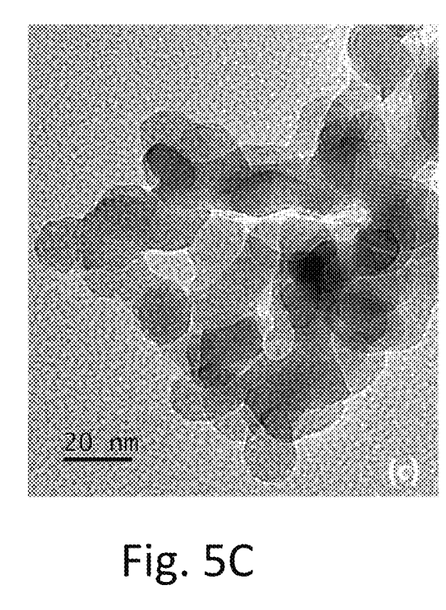
FIGS. 5C and 5D are TEM images of $Ca_2GeO_4$:Cr nanophosphor powders obtained at 700° C.
Figure 5D:
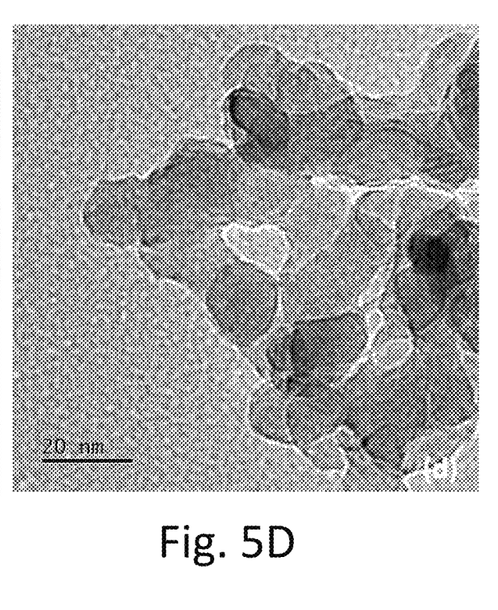

FIGS. 5A and 5B are transmission electron microscope (TEM) images of $Ca_2GeO_4$:$Cr^{4+}$ nanoparticles obtained at 950° C., while FIGS. 5C and D are those obtained at 700° C. The average nanoparticle diameter is decreased from 100~200 nm in the former case to 10-20 nm in the latter case. The pH value of the mixed solution and ratio of L-tartaric acid to Ge ions can be optimized to obtain the pure $Ca_2GeO_4$ phase and reduce the particle size to <50 nm at a lower calcination temperature such as 700-750° C.

Figure 6A:
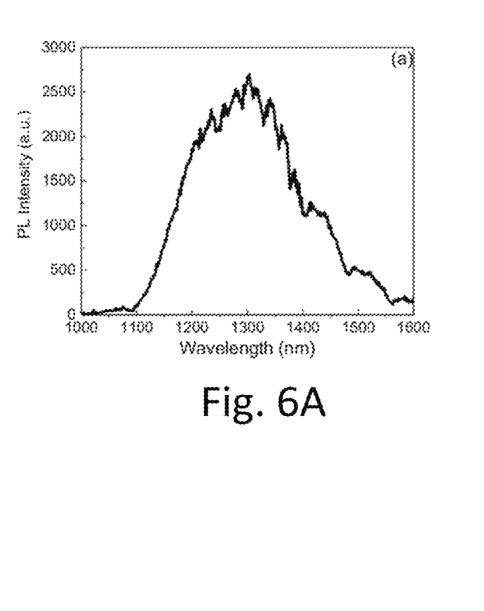
FIG. 6A is a room-temperature photoluminescence (PL) spectrum.
Figure 6B:
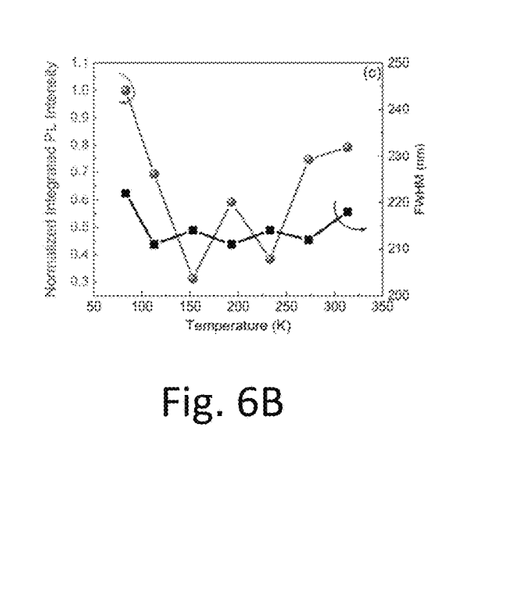
FIG. 6B illustrates temperature-dependent photoluminescence spectra.
Figure 6C:
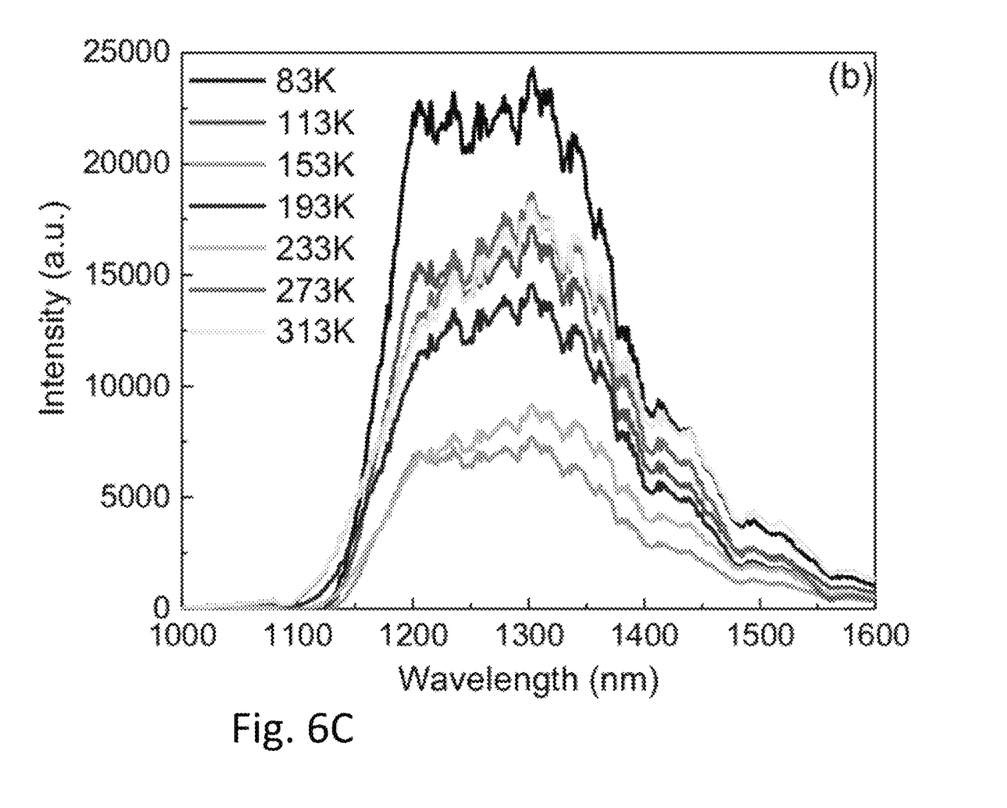
FIG. 6C illustrates normalized integrated PL intensity and PL spectral width FWHM as a function of temperature. The samples were annealed at 950° C. and under an excitation wavelength of 633 nm.

FIGS. 6A, B, and C illustrate optical properties of $Ca_2GeO_4$:0.05 Cr. Room-temperature photoluminescence (PL) in FIG. 6A spans from 1100 nm to 1600 nm, covering most of the NIR-II window. The peak position lies at 1300 nm, confirming that the $Cr^{4+}$ emission centers are optically active. FIGS. 6B and 6C reveal the temperature-dependent PL behavior, quite different from single crystal $Cr^{4+}$-doped $Ca_2GeO_4$. The full width half maximum (FWHM) of the PL spectra is kept at roughly 200 nm, independent of the temperature. The integrated PL intensity of nanophosphor does not follow the monotonic decrease with the increase of temperature. Instead, the integrated PL decreases first when the temperature raises from 83 K to 233 K, then gradually increases beyond the room temperature. The absence of thermal quench at body temperature (37° C. or 310K) make these nanoparticles especially attractive for in vivo applications. Some reports show the defects formed in germinate hosts ($Ca_2GeO_4$, $Ca_2Ge_7O_{16}$) can act as carrier trapping centers leading to visible persistent emission. We plan to examine the persistent afterglow performance of $Ca_2GeO_4$:Cr, which could extend the persistent luminescence to NIR II range. The advantage of briefly-persistent NIR-II is we can eliminate the autofluorescence and reduce the background noise in the optical bio-imaging by gated image capture in windows following pulses of the X-Ray or other radiation used to stimulate the phosphor.

Example 2

$Ca_2GeO_4$:$Cr^{4+}$ Nanophosphor Coated with Silica Shell

The synthesized $Ca_2GeO_4$:Cr nanophosphor powder of example 1 was coated with a silica shell for surface passivation. First, $Ca_2GeO_4$:$Cr^{4+}$ powder was dispersed into colloidal silica suspension with a molar ratio of silica to $Ca_2GeO_4$ powder in the range of 0.001~0.1. Then the suspension was stirred at room temperature followed by a washing procedure. The final core-shell powder is obtained after drying at 700~900° C. The thickness and mesoporosity of the silica shell are determined by colloidal silica size and concentration. The enhancement in PL intensity and the increase in the decay time of core-shell powders can be achieved using this method.

Example 3

$Ca_5Ge_3O_{11}$:$Cr^{4+}$ Nanophosphor Synthesis

Figure 7:
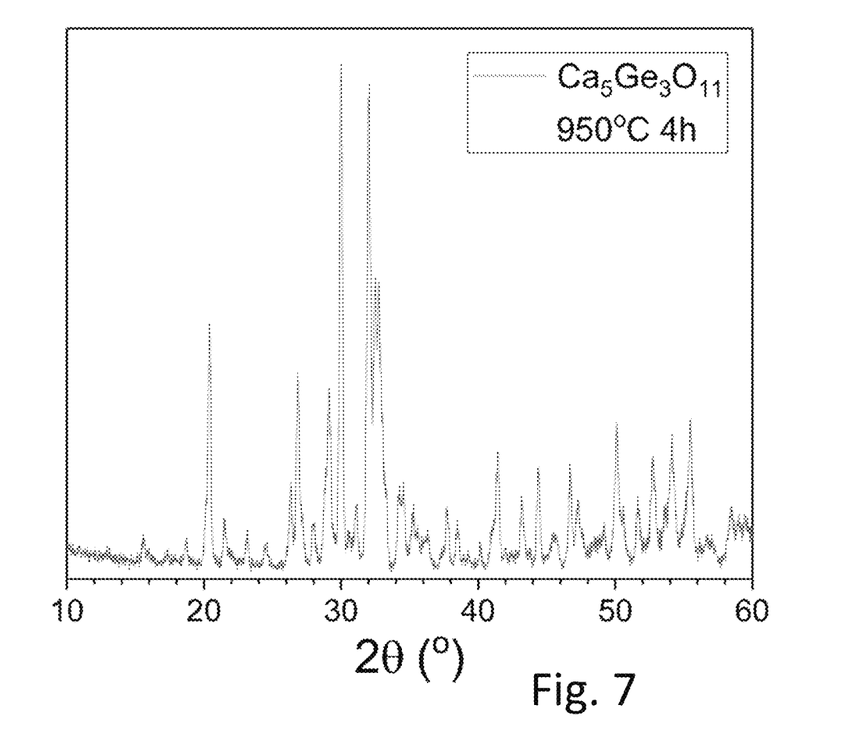
FIG. 7 illustrates X-ray diffraction patterns of the pure-phase $Ca_2GeO_4$:Cr nanopowder annealed at 950° C.

Following the similar procedure in example 1, $Ca_5Ge_3O_{11}$:$Cr^{4+}$ pure-phase nanophosphor is synthesized with the molar ratio L-tartaric acid/Ge of 8:1 and PH of 0.3 FIG. 7 exhibits the X-ray diffraction pattern of pure $Ca_5Ge_3O_{11}$ phase obtained at 950° C. All peak positions in good agreement with triclinic crystal structure of $Ca_5Ge_3O_{11}$. The small amount of $Cr^{4+}$ dopant (molar ratio of Cr to Ge of 0.01) affect the host crystal structure negligibly.

Example 4

Figure 8:
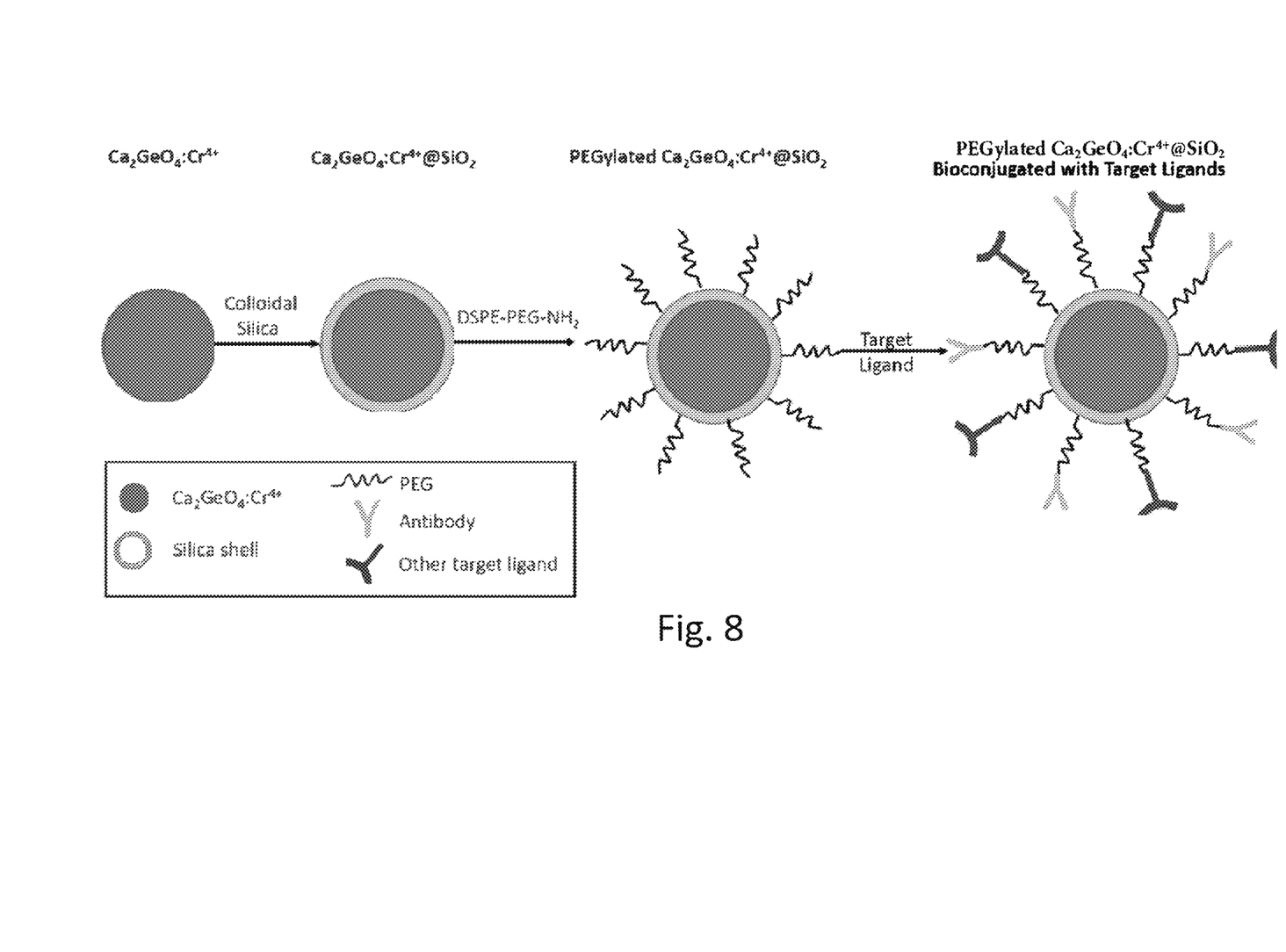
FIG. 8 illustrates a schematic protocol for preparation of surface modified $Ca_2GeO_4$:Cr nanopowder core/shell structures for optical bio-imaging diagnosis applications.

PEGylated $Ca_2GeO_4:Cr^{4+}$@Silica Core/Shell Nanophosphor for Optical Bioimaging FIG. 8 illustrates a schematic protocol of nanophosphor surface modification for optical bio-imaging diagnosis application. The as-prepared $Ca_2GeO_4:Cr^{4+}$@silica core/shell nanophosphors described in Example 2 are further treated with phosphatidylethanolamine(DSPE)-polyethylene glycol(PEG)-ammonia($NH_2$) to modify the surface of the nanoparticles such that it becomes a hydrophilic surface. The PEG functionalization can minimize the nonspecific interactions of nanophosphor with protein and increase the in vivo circulation time. Meanwhile, it enables nanophosphors usable in biologically relevant media and offers a platform for bioconjugation of targeting ligands, such as antibodies. To obtain hydrophilic PEGylated nanophosphor, $Ca_2GeO_4:Cr^{4+}$@silica core/shell particles are dispersed in deionized water by sonication for 3 hrs. DSPE-PEG-$NH_2$ or PEG is then added into the suspension mixture and stirred for 20 hrs. The weight ratio of nanophosphors, deionized water, and PEG is 1:10:10. The resulting PEG-modified nanophosphor is washed three times with deionized water to remove PEG residue and further filtered by 0.3 μm syringe filters to eliminate large particles. The PEGylated nanophosphors can be decorated with specific molecular ligands for active targeting applications by means of chemical reaction, ligand exchange, ligand-ligand interaction, etc. For example, by introducing the folate (FA) ligand to replace —$NH_2$ toward aqueous solution on the surface of the nanophosphors, we can facilitate the specific binding of nanophosphors to folate receptor positive tumor cells for optical targeted bioimaging diagnosis.

Example 5

Figure 9:
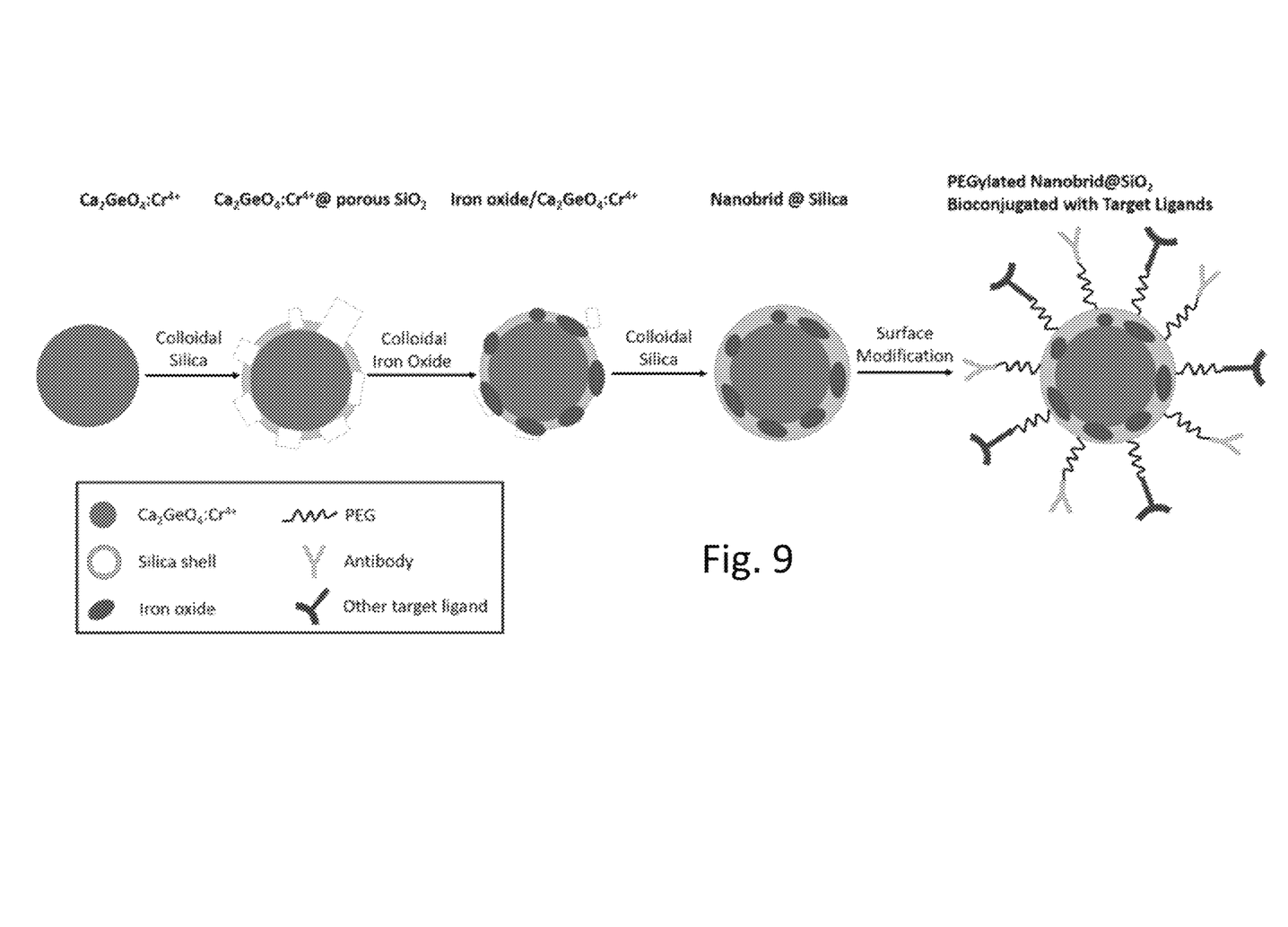
FIG. 9 illustrates a protocol for preparation of surface modified iron oxide/$Ca_2GeO_4$:$Cr^{4+}$ nanobrids@silica structure for bimodal bioimaging diagnosis applications.

$\gamma$-$Fe_2O_3$/$Ca_2GeO_4:Cr^{4+}$ Nanobrids for Bimodal Bio-imaging Diagnosis The magnetic resonance imaging (MRI) negative contrast properties provide a high spatial resolution. Bimodal bio-imaging diagnosis can be achieved by combining both the advantages of MRI and optical properties of iron oxide/$Ca_2GeO_4:Cr^{4+}$ nanobrids. FIG. 9 exhibits a schematic protocol for surface modified iron oxide/$Ca_2GeO_4:Cr^{4+}$ nanobrids@ silica. Following example 2, a mesoporous silica shell is formed around $Ca_2GeO_4:Cr^{4+}$ nanophosphor by choosing the appropriate colloidal silica size and concentration. Ultrasmall superparamagnetic $\gamma$-$Fe_2O_3$ nanoparticles are then embedded in the mesoporous silica shell with colloidal iron oxide, similar to the method of colloidal silica. Another silica shell is coated to cover iron oxide nanoparticles. The weight ratio of iron oxide to $Ca_2GeO_4:Cr^{4+}$ nanophosphor is 5%~50%. The size of iron oxide nanoparticle is in the range of 5~20 nm. The magnetic iron oxide labeling enables MRI tracking and targeting. Further surface modification for the optical targeted bioimaging diagnosis can be obtained on the surface iron oxide/$Ca_2GeO_4:Cr^{4+}$ nanobrid@ silica shell functionalized with target ligands.

Example 6

$Ca_2GeO_4:Cr^{4+}$@Silica Core/Shell Nanophosphor for Targeted Photothermal Therapy One example for the treatment of cancers is the targeted photothermal therapy using the heat (ideally beyond 42° C.) generated from the light radiation to destroy cancer cells. The inorganic materials for photothermal agents include metallic nanostructures (Au, Ag) and metal oxide nanoparticles ($Fe_3O_4$). Following the similar preparation protocol described in FIG. 9, colloidal $Fe_3O_4$ or Au nanoparticles are employed for conversion laser radiation to heat. Additional advantages of use of Au nanostructures is the plasmon-enhanced absorption. Meanwhile, it is possible to enhance $Ca_2GeO_4:Cr^{4+}$ emission by engineering Au nanostructures.

Application to Medical Imaging

Figure 10:
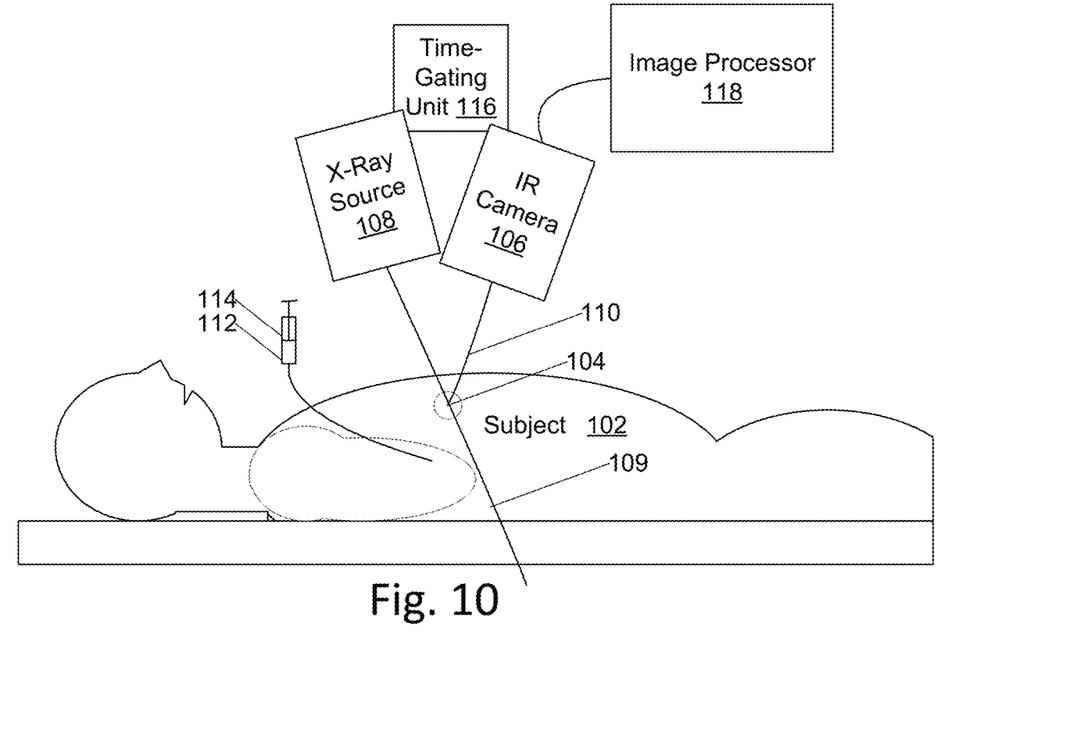
FIG. 10 illustrates a system for medical imaging using injected surface modified $Ca_2GeO_4$:Cr nanopowder core/shell structures with X-Ray stimulus and an infrared imaging camera.

A medical imaging system for imaging in a subject 102 is illustrated in FIG. 10. The subject, having a suspect tissue such as a tumor 104, is positioned with an infrared camera 106 positioned to image tumor 104. An X-Ray radiation source 108 is positioned to provide a radiation beam 109 that intersects tumor 104. A suspension of the PEGylated $Ca_2GeO_4:Cr^{4+}$@silica core/shell nanophosphor 112 tagged with tissue-selective molecules such as antibodies, nucleic acids, or other ligands is positioned in an injection apparatus 114 and injected into subject 102. The nanoparticles with tissue-selective molecules are given time to bind with tumor 104. X-Ray source 108 is activated, providing radiation beam 109 intersecting tumor 104, causing the nanoparticles to phosphoresce, providing NIR-II light that passes through skin and other tissue of subject 102 to infrared camera 106, where the light is imaged.

In an embodiment, a time-gating control unit 116 is provided to synchronize infrared camera 106 to pulses of the X-ray beam 109. In an embodiment, time-gating control unit 116 controls infrared camera 106 such that camera 106 is time-gated to perform imaging of near infrared light immediately after, but not during, pulses of the X-ray beam 109 to reduce interference from autofluorescence of the subject's tissues. In an embodiment, a digital image processing system 118 is provided to capture and enhance the near-infrared images captured by camera 106.

In embodiments, the nanophosphor is stimulated by light from Cherenkov emissions from either an X-ray or charged-particle beam, in addition to direct stimulation from the beam itself.

In a particular embodiment, in order to provide enhanced imaging, the radiation beam is swept across tumor 104 either by sweeping a collimator at X-ray source 108 or, as in a computed tomography (CT) scanner, rotating X-ray source 108 while camera 106 is configured to capture a sequence of images of the infrared light emitted by the nanophosphor in subject 102 and bound to tumor 104. In this embodiment, the nanophosphor used has a short persistence time, 100 milliseconds or less, so that each image of the sequence of images corresponds to a particular position and/or angle of the radiation beam so that a sequence of images can be obtained using different beam positions and/or angles. In an embodiment using a rotating X-ray source 108, a reconstruction algorithm similar to those used in CT scanner is used to generate a three-dimensional image of tumor 104 and surrounding tissues in subject 102.

Figure 11:
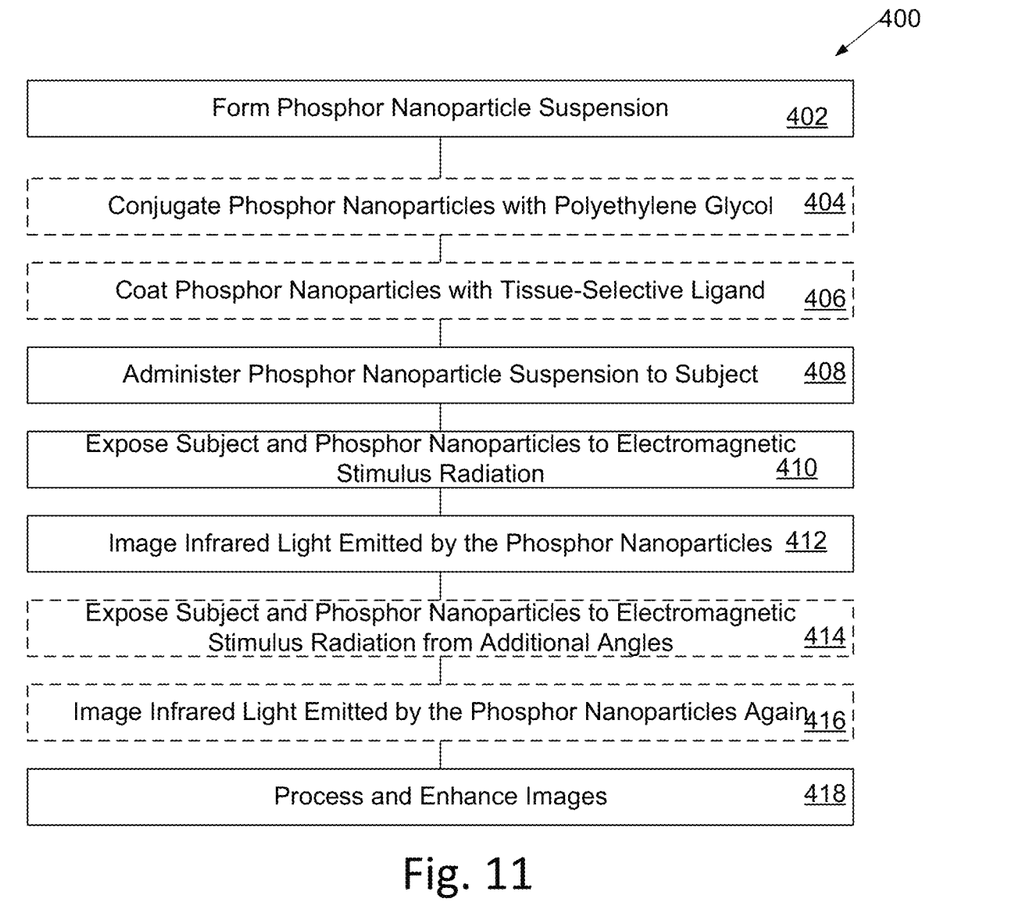
FIG. 11 is a block diagram of a method of medical imaging using the $Ca_2GeO_4$:Cr phosphor nanoparticle nanopowder.

Putting the imaging method together, the method 400 (FIG. 11) of medical imaging begins with forming 402 the phosphor nanoparticle suspension. The nanoparticle suspension may be tagged by PEGylated with polyethylene glycol 404 and coated 406 with tissue-selective ligands before being administered 408 to a subject where the tagged phosphor nanoparticles may concentrate in a particular organ or tumor. The subject and tumor, with the phosphor nanoparticles, is then exposed to 410, or illuminated, with a beam of stimulus radiation that in embodiments is electromagnetic stimulus radiation consisting of X-ray radiation or blue light. In alternative embodiments the subject and tumor, with the phosphor nanoparticles, may be exposed to a particle beam that forms blue-light Cherenkov electromagnetic stimulus radiation upon interacting with tissue of the subject. Near-infrared light emitted by stimulated phosphor nanoparticles is then emitted from the subject and imaged 412 with a gated infrared camera. The subject may be illuminated with additional beams of X-ray radiation or particle beams having different beam shape or position, or beams of X-ray radiation or particle beams arriving at the subject and tumor from at least a second or additional positions or angles, to expose 414 the subject and tumor differently and additional images 416 are taken. In an exemplary embodiment, a narrow fan-beam of X-ray radiation is used and swept across the subject and tumor, the long-wavelength or infrared images of the subject in this embodiment effectively images a sequence of slices of different depths below surface of the subject and thus gives three-dimensional information regarding the subject or tumor in the subject; in another exemplary embodiment an X-ray radiation source is rotated about the subject and scanned along the subject in the manner of a CT machine, illuminating the subject and tumor with beams from multiple positions and angles while imaging is performed. The long-wavelength or infrared images may then be processed 418 to enhance them and provide significantly improved 3-dimensional images of, or a three-dimensional model of, the tumor to allow evaluation of possible treatments of the tumor.

Changes may be made in the above methods and systems without departing from the scope hereof. For example, although machine 100 is illustrated with a bevel head apparatus 125, other configurations for holding and manipulating torch 120 may be used. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method of imaging a tumor in a subject comprising:
    administering tetravalent Cr-doped nanophosphor to the subject, the tetravalent Cr-doped nanophosphor excitable by stimulus electromagnetic radiation comprising at least one of X-ray and blue light;
    exposing the subject and the tetravalent Cr-doped nanophosphor to stimulus electromagnetic radiation to excite the tetravalent Cr-doped nanophosphor with a first beam position and from a first beam angle; and
    imaging long wavelength light emitted by tetravalent Cr-doped nanophosphor and emitted by the subject.

2. The method of imaging of claim 1, the tetravalent Cr-doped nanophosphor being coated with a tissue-selective ligand, the tissue-selective ligand configured to bind to the tumor.

3. The method of claim 2 wherein the tetravalent Cr-doped nanophosphor coated with a tissue-selective ligand comprises a PEGylated silica-coated tetravalent Cr-doped nanophosphor.

4. The method of claim 1 wherein the long wavelength light emitted by the subject is near infrared light.

5. The method of claim 4 wherein the long wavelength light is imaged with a camera having shutter timing synchronized to pulses of the stimulus electromagnetic radiation.

6. The method of claim 5 wherein exposing the subject and the tetravalent Cr-doped nanophosphor to stimulus electromagnetic radiation comprises exposing the subject to a focused beam of the stimulus electromagnetic radiation.

7. The method of claim 6 further comprising exposing the subject and tetravalent Cr-doped nanophosphor to stimulus electromagnetic radiation from at least a second beam position at a second beam angle, where at least one of the second beam position or angle differs from the first beam position or angle.

8. The method of claim 5 further comprising image processing to reconstruct a three dimensional model of the tumor.

9. The method of claim 6 wherein the tetravalent Cr-doped nanophosphor comprise primarily of phosphor having a chemical formula $(M)x(Ge_1N)yOz:Cr^{4+}$ where M is one or more elements selected from the group consisting of calcium (Ca), magnesium (Mg), strontium (Sr), barium (Ba), and zinc (Zn) and N is one or more elements selected from the group consisting of germanium (Ge), silicon (Si), and tin (Sn), and the $Cr^{4+}$ is chromium substituted for less than five percent of N.

10. The method of claim 9, the tetravalent Cr-doped nanophosphor comprising phosphor primarily having chemical formula $Ca_2GeO_4:Cr^{4+}$.

11. The method of claim 9, the tetravalent Cr-doped nanophosphor comprising phosphor primarily having chemical formula $Ca_5Ge_3O_{11}: Cr^{4+}$.

12. The method of claim 9, the tetravalent Cr-doped nanophosphor having particle size of less than 200 nanometers diameter.

13. The method of claim 12, each tetravalent Cr-doped nanophosphor having a silica coating.

14. The method of claim 13, the tetravalent Cr-doped nanophosphor comprising nanoparticles conjugated with polyethylene glycol and tissue selective compounds selected from the group consisting of antibodies, and nucleic acid chains.

15. The method of claim 9 wherein the electromagnetic radiation is an X-ray beam and the long wavelength light is near infrared light emitted from the subject.

16. The method of claim 15, further comprising time-gating the imaging of near infrared light immediately after pulses of the X-ray beam.

* * * * *